US00RE35113E

United States Patent [19]

Grim

[11] E Patent Number: Re. 35,113

[45] Reissued Date of Patent: Dec. 5, 1995

[54] ORTHOPAEDIC GEL PAD ASSEMBLY

[75] Inventor: Tracy E. Grim, Broken Arrow, Okla.

[73] Assignee: Royce Medical Company, Camarillo, Calif.

[21] Appl. No.: 227,187

[22] Filed: Apr. 13, 1994

Related U.S. Patent Documents

Reissue of:

[64] Patent No.: 5,027,801
Issued: Jul. 2, 1991
Appl. No.: 470,140
Filed: Jan. 25, 1990

U.S. Applications:

[63] Continuation of Ser. No. 987,622, Dec. 12, 1992, abandoned.

[51] Int. Cl.[6] ..... A61F 5/00

[52] U.S. Cl. ..... 602/14; 602/23; 602/27

[58] Field of Search ..... 602/19, 20, 23, 602/26, 27, 2; 128/892, 893, 402, 403

[56] References Cited

U.S. PATENT DOCUMENTS 3,548,420 12/1970 Spence .
3,885,403 5/1975 Spencer .
4,230,101 10/1980 Gold ..... 602/19
4,243,041 1/1981 Paul ..... 602/2
4,280,489 7/1981 Johnson, Jr. .
4,517,968 5/1985 Greene et al. ..... 602/26
4,572,169 2/1986 Mauldin et al. .
4,590,932 5/1986 Wilkerson ..... 602/26
4,628,945 12/1986 Johnson, Jr. .
4,671,267 6/1987 Stout ..... 602/2

FOREIGN PATENT DOCUMENTS 0162583 11/1985 European Pat. Off. ..... 128/403

*Primary Examiner*—Richard J. Apley
*Assistant Examiner*—Lynne A. Reichard
*Attorney, Agent, or Firm*—Poms, Smith, Lande & Rose

[57] ABSTRACT

An orthopaedic gel pad assembly includes a layer of gel, with a backing layer behind it, an apertured pad extending around the layer of gel and a thin plastic film extending over the front surface of the gel. The plastic film controls the configuration of the front face of the gel, and the gel may be recessed, or indented, and may protrude forwardly out from the apertured pad. Stiff orthopaedic supports may be provided to back up the gel pad unit.

26 Claims, 3 Drawing Sheets

FIG. 10
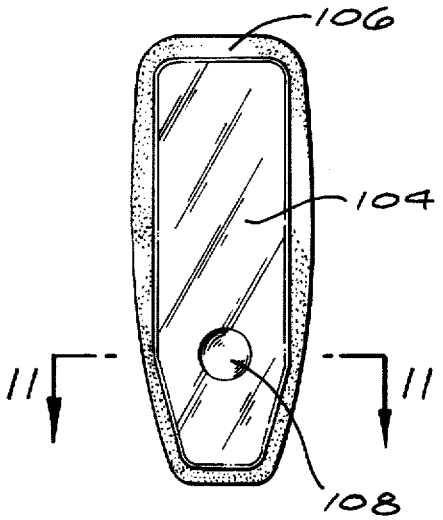
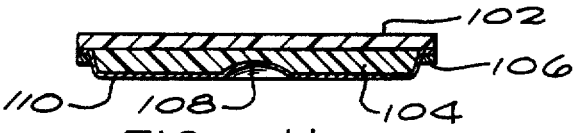
FIG. 11
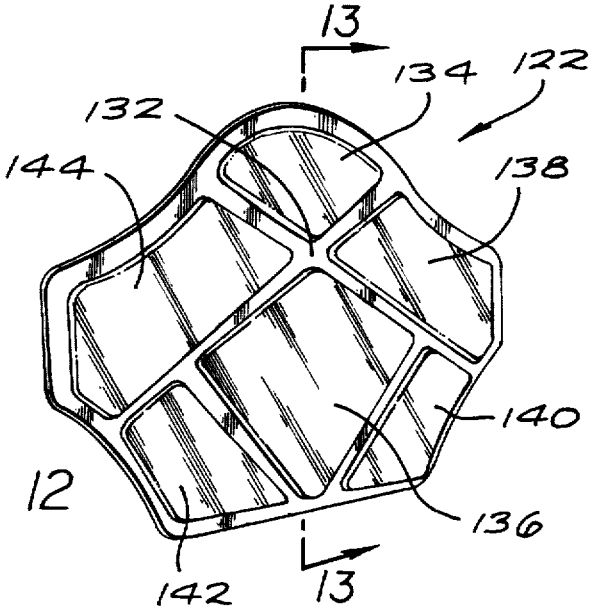
FIG. 12
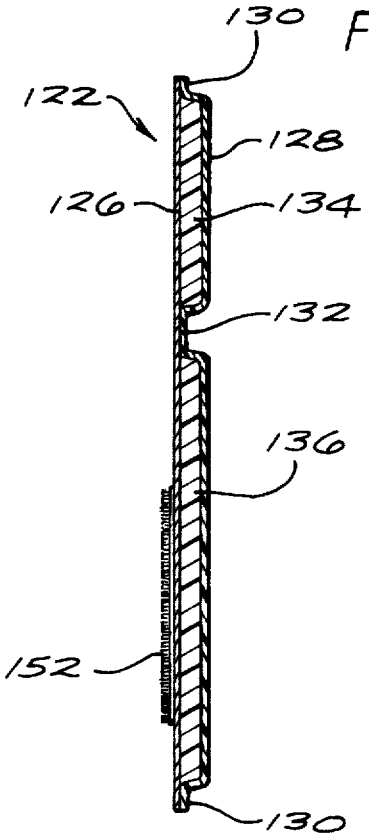
FIG. 13
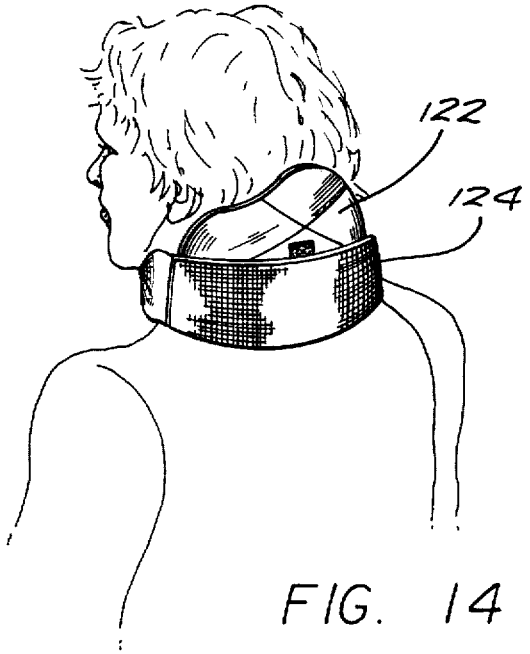
FIG. 14

ORTHOPAEDIC GEL PAD ASSEMBLY

Matter enclosed in heavy brackets [ ] appears in the original patent but forms no part of this reissue specification; matter printed in italics indicates the additions made by reissue.

*This application is a continuation of U.S. patent application Ser. No. 07/987,622 filed Dec. 12, 1992, now abandoned, which is a reissue of U.S. patent application Ser. No. 07/470,140 filed Jan. 25, 1990, now U.S. Pat. No. 5,027,801.*

RELATED PATENT APPLICATIONS

Attention is directed to U.S. patent application Ser. No. 055,711, filed May 29, 1987, now U.S. Pat. No. 4,844,094, granted July 4, 1989, entitled "Ankle Brace" and assigned to the assignee of this application; and to U.S. patent application Ser. No. 168,681, filed Mar. 16, 1988, now U.S. Pat. No. 4,913,755, granted Apr. 3, 1990 and also assigned to the assignee of this application. This patent application is a continuation-in-part of the foregoing two patent applications.

BACKGROUND OF THE INVENTION

After injury to an ankle, such as a fracture or severe ankle sprain, it may be necessary to completely immobilize the ankle through the use of a molded plaster or resin cast. However, once the injury has been stabilized, recovery may be hastened by removing the molded plaster or resin cast and using a removable functional walking brace so that the ankle can be exercised during healing.

An important element of these functional walking braces is the liner element that provides a resilient support against the sides of the ankle. The liner helps stabilize the ankle against inversion and eversion while still permitting the normal dorsi-flexion and plantar-flexion movement of the; ankle. It has previously been proposed to form such pads of foam rubber, or using inflatable bags.

One such proposed prior ankle brace using an air-inflatable liner is shown in prior U.S. Pat. No. 4,280,489 listing Glen W. Johnson, Jr. as the inventor. Although the air-inflatable liner provides some resilient support against the ankle, it suffers from the following disadvantages. One disadvantage is that the air is unduly buoyant, and permits rapid movement of the air from one side to another, so that adequate support is not provided. Further, with air inflatable bladders, a puncture renders the braces inoperative and dangerous to the user as the outer rigid plastic shells could cut or rub the wearer.

The use of foam rubber pads, as exposed liners in walking braces is disclosed in U.S. Pat. No. 4,572,169 listing Mauldin and Jones as inventors. The use of foam rubber has significant disadvantages in that the foam rubber is U.V. sensitive, and tends to deteriorate after exposure a certain period of time. Further, the foam does not tend to conform to the configuration of the ankle joint, but bounces back to its original configuration. Also, neither air filled cushioning arrangements nor foam are suitable for hot and cold temperature therapy.

Attention is also directed to W. R. Spence U.S. Pat. No. 3,548,420 granted Dec. 11, 1970, which discloses the use of gel in a "Cushion Structure", but not in combination with a thin enclosing plastic layer.

Accordingly, the objects of this invention include providing an orthopaedic brace or support that provides resilient support and is free from adverse effects of puncturing, forms a relatively stable pad, conforms to the configuration of the ankle, has a high thermal capacity, has well defined boundaries, has homogeneous thickness throughout its length and width, and is very comfortable when used for therapeutic heating or chilling of the injured leg, and has good long term hot and cold therapy properties.

SUMMARY OF THE INVENTION

The present invention is directed to a method and an apparatus for forming gel-filled cushion pads that provide a resilient support against the ankle. The apparatus includes, among other elements, a vacuum chamber that is substantially enclosed except at the top. A perforated plate having many drilled, small holes on its surface is used to cover the top portion of the vacuum chamber. The vacuum chamber also includes a channel for connecting it to a vacuum pump. A vacuum pump is used to withdraw the air from the vacuum chamber.

A spacer pad, normally made of foam rubber is then laid over the perforated plate. The spacer pad normally includes one or more openings on its surface. Each of these openings provide for a space that has the perforated base plate as its base and has a depth equal to the thickness of the spacer pad. Further, the walls of this space have the pattern of the corresponding opening on the surface of spacer pad.

The present invention also includes a front aperture pad that is normally made of rubber foam, and overlies the space pad. The front aperture pad also has openings on its surface that normally have the same pattern as the openings on the surface of the spacer pad. The front aperture pad is normally laid over on the spacer pad such that these openings on the spacer pad are in alignment with openings on the spacer pad on that pad. With the openings on the aperture pad and spacer pad aligned, a laterally enclosed space is formed. This space is laterally confined at the bottom by the perforated base plate, and is laterally confined by the inner walls of the spacer pad and front pad. The depth of this space is substantially equal to the sum of one thickness of the spacer pad and one thickness of the front pad. This space, hereinafter called "the gel-space" is used for storing the liquid gel for the solidification process.

Another element of the apparatus is a thin plastic film which may, for example, be made of urethane. With the front pad in alignment with the spacer pad, an adhesive coating is located on the upper surface of the front pad and a thin film of urethane is laid over the front pad. Then, the vacuum pump is turned on, causing air to be drawn from the vacuum chamber. The fine perforations through the base plate extend to the aligned openings in the two pads within the periphery of these openings. As a result, a stream of air flows into the vacuum chamber through the exposed holes on the surface of the perforated base plate. The inflow of air through these holes causes the thin film to be drawn towards the perforated plate tightly and neatly particularly around the edges of the gel-receiving openings. Concurrently with this vacuuming process, a heating device is used to raise the temperature of the thin film and thereby cause it to expand and snugly cover the exposed base plate as well as the walls of the gel-space. After the heating process, the thin film substantially forms the boundaries of the gel-space. A predetermined amount of the gel is then mixed so that it will solidify in a few minutes, and is poured into the gel-space, on top of the thin film, and allowed to solidify for a few minutes. The predetermined amount of gel is measured to substantially fill the gel-space.

The vacuum process may continue while the liquid gel is being poured into the gel-space to make sure that the thin film will not be substantially displaced.

After the gel has solidified, an adhesive coated back pad, normally made of foam rubber, is laid over on top of the thin plastic film.

With this process, a solid, dense layer of gel is confined between the back pad on the top and the thin film at the bottom, with the thin film being secured to the inner walls of the spacer pad and front pad. Each one of the gel filled gel-spaces constitutes a gel pad unit. Since several contiguous gel-spaces may be formed by overlying the front pad on the spacer pad, the above process may involve formation of several contiguous gel pad units Since a number of contiguous gel pad units my be formed concurrently during the above process, these gel pad units my be cut out to form a single unit Each individual unit of these gel cushion pads or linen may then be used in walking braces for providing a resilient support against the ankle. By using these gel linen for each walking brace, multiple advantages are realized.

First, a gel cushion pad may be repeatedly punctured with no adverse effect, as the gel seals itself and does not leak out. Further these gel liners form a relatively stable pad in which the gel does shift in position somewhat to conform to the configuration of the ankle bone, but does not migrate more than about one-quarter or one inch.

In addition, gel liners produced by the method of the present invention have n well defined boundary and homogeneous thickness throughout the length and width of the gel pad. Further, since the gel pad covers only the injured part of the leg, the rest of the leg will not be unnecessarily affected by the heat and cold therapeutic treatment received by the injured part of the leg.

It is further noted that the gel pads may be formed by the method of the present invention, using a somewhat thicker spacer pad, and having a backing in the form of an additional urethane film or layer, heat sealed or adhered to the underlying urethane layer to form a simple urethane film covered layer, similar to that shown in the prior copending patent application cited hereinabove.

In accordance with another aspect of the invention, an orthopaedic assembly includes a gel pad employed in combination with stiff supporting arrangements for splinting a bone or joint, with the gel pad being secured to the stiff supporting arrangements to match the irregular and individual configuration of the joint or bone to which the orthopaedic assembly is to be secured. These arrangements are applicable to the wrist, knee, and other bones or joints, as well as to the ankle.

The combination of gel, an inner protective plastic film, and a backing layer, which may, for example, be formed of foam rubber, provides excellent overall properties for use with a brace or support, with the gel pad adjacent the injured area, such as a joint, to conform thereto, and the foam rubber providing resilient support, and also having good thermal insulation properties when the gel is heated or cooled to provide hot or cold therapy. Further, the inner film protects the gel from contamination and the user's body from the stickiness of the gel. Also, the inner film permits configuration of the gel to the desired contour or shape, with gel-free spaces to permit easy flexing of the pad, or reduced thickness gel areas to accommodate protruding bone structures, such as the malleolus.

Other objects, features, and advantages of the invention will become apparent from n consideration of the following detailed description and from the accompanying drawings

BRIEF DESCRIPTION OF THE DRAWINGS

FIG. 10 shows a modified form of the pad shown in FIGS. 4 through 6;

FIG. 11 is a cross-sectional view taken along line 11—11 of FIG. 10;

FIG. 12 is a perspective view of a gel pad which may be used with a neck brace or support;

FIG. 13 is a cross-sectional view taken along line 13—13 of FIG. 12; and FIG. 14 shows the gel pad of FIGS. 12 and 13 in use with a neck brace.

DETAILED DESCRIPTION

Figure 1:
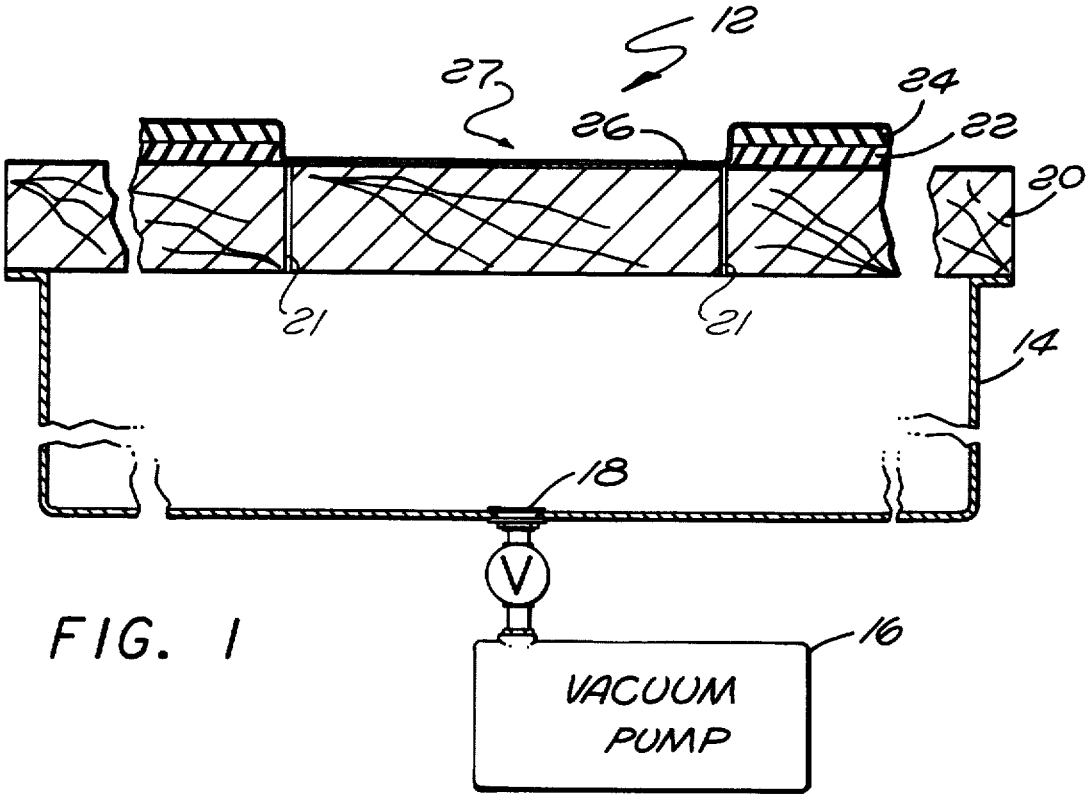
FIG. 1 is a cross-sectional view of an apparatus for forming gel-filled cushion pad or liners, illustrating the principles of the invention.

Referring more particularly to the drawings, FIG. 1 is a cross-sectional view of an apparatus 12 for forming gel liners, illustrating certain principles of the invention. As shown, the apparatus includes a vacuum chamber 14 that is substantially enclosed, except at the bottom opening-channel 18 and the top opening. Vacuum chamber 14 is connected to a vacuum pump 16 using the channel 18. When the vacuum pump 16 is turned on, the air is drawn through channel 18, out of chamber 14. The opening at the top of the chamber 14 is substantially covered by a perforated plate base 20 having a number of drilled holes on its surface. In this manner, the vacuum created in the chamber 14, causes streams of air to flow into the chamber 14 through the fine holes extending through the surface of the perforated plate base 20.

Figure 3:
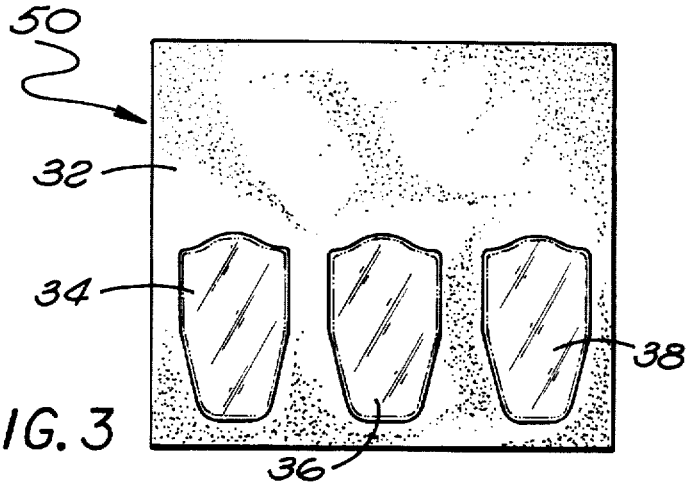
FIG. 3 is a top view of the finished product that includes three contiguous units of gel pad liners.

The apparatus also includes a spacer pad 22 which overlies the perforated base plate 20. Spacer pad 22 is relatively thin, and may have a thickness of about 3 milllmeters. The spacer pad 22 may be made of rubber foam material. As shown in FIG. 3, the spacer pad 22 may have three patterned openings, each used for forming an individual and contiguous unit of gel-filled cushion pad. As shown in FIG. 1, a front aperture pad 24 overlies spacer pad 22. Normally, spacer pad 22 and the from pad 24 include substantially similar and aligned patterned openings on their surface. This is better illustrated in FIG. 3 showing substantially similar patterned openings on the surface of spacer pad 22 and front pad 24. Thus, by overlying front pad 24 on spacer pad 22 in such a way that the patterned opening of the front pad 24 and spacer pad 22 are in alignment, several "gel-pockets" or "gel-spaces" are formed, such as gel-pocket 27.

The gel-pocket 27 is enclosed laterally by the inner walls of front pad 24 and spacer pad 22. Further, as shown in FIG. 1, the front pad 24 has substantially the same thickness as that of the spacer pad 22. Of course, the two pads may have unequal thicknesses depending on the needs of a particular application. In addition, the front pad may also be formed of rubber foam material. A thin layer of a plastic or urethane film 26 is then laid over the front pad 24. Adhesive material is used to hold the thin film 26 over the front pad 24. With the vacuum pumps 16 being turned on, air will be sucked out of chamber 14 through channel 18. The displaced volume of air is replaced by the streams of air that flow into chamber 14 through the holes 21 extending through the perforated plate 20 adjacent the edges of the gel opening. The suction of air through openings 21 into chamber 14 causes the thin film 26 to be firmly drawn into contact with perforated plate 20 and conform to the inner walls of spacer pad 22 and front pad 24.

A heating device is then used to heat the thin film 26 so that thin film 26 will readily conform to the shape of the perforated base plate as well as to the inner walls of spacer pad 22 and front pad 24. Gel-space 27 is formed by substantially conforming the thin film 26 to the shape of perforated base plate and the inner walls of front pad 24 and spacer pad 22. The vacuum pump 16 may continue to run in order to keep the thin film 26 in place. With thin film 26 kept tightly in place, a predetermined amount of liquid gel is then poured into the gel-space 27 to substantially fill up the gel-space. (See FIG. 2). The liquid gel is allowed to cool off to form a semi-solid and resilient gel pad layer.

Figure 2:
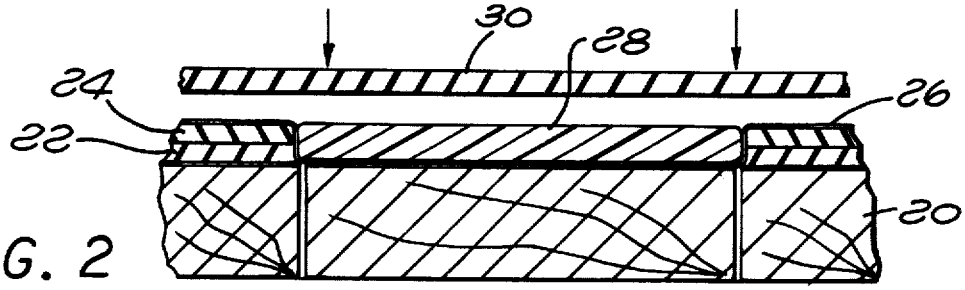
FIG. 2 is a partial cross-sectional side view of the apparatus of FIG. 1 further illustrating the formation of the gel-pads.

FIG. 2 is a partial cross-sectional side view of apparatus 12 of FIG. 1 further illustrating the relative position of the gel pad with respect to the rest of the assembly. As shown in FIG. 2, the gel layer 28 substantially fills up the gel space 27. When the gel layer 28 solidifies within a short period of time, the depth of the gel layer 28 is substantially equal to the total thickness of spacer pad 22 and front pad 24. Then, the back pad 30 which may have adhesive material spread over its bottom surface, may be overlaid onto the thin film 26 and gel layer 28. The adhesive material causes the back pad 30 to firmly adhere to the urethane layer 26, sealing the gel material in the product formed by the urethane film and the back pad. At this point, the process of forming gel pads is substantially completed.

At this stage, the assembly includes multiple layers, namely, the back pad layer 30, the gel layer 28, the front pad layer 24, the urethane layer 26, and the spacer pad, 22. All layers except for the spacer pad layer 22 are confined or tightly held together using adhesive material. More specifically, the front pad is adhesively secured to the urethane layer on one side of the urethane layer, and the back pad is adhesively secured to the other side of the urethane layer. Further, the semi-solid layer of gel 28 is confined between the urethane layer 26 on one side and to the back pad 30 on the other side. The spacer pad 22 is not connected to any of the other layers and may be left behind when the remainder of the assembly is lifted up, after the vacuum is released. The purpose of spacer pad 22 was to help form the gel-pocket for forming of the gel pad.

FIG. 3 is a top view of the intermediate product 50 that includes three contiguous units of gel pads. As shown in FIG. 3, three gel cushion pads, namely, cushion pads 34, 36 and 38 have been formed by the process described above. Obviously, the number of the contiguous gel pads may be increased by including more patterned openings on the surface of the spacer and front pads. Further, the pattern may be varied according to the needs of a particular .application. The next step involves cutting out each individual unit so that they may be used individually in a walking brace. (See FIG. 4).

Figure 4:
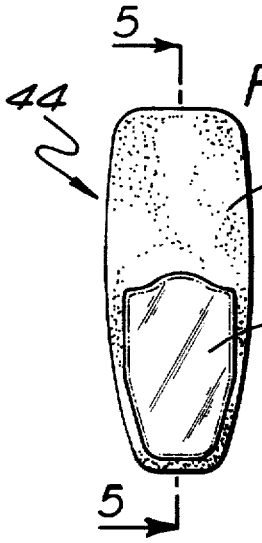
FIG. 4 is a top view of an individual gel-pad unit that is cut out of the finished product shown in FIG. 3.

FIG. 4 is a top view of an individual gel liner unit 44 after it has been cut out of the composite pad 50 of FIG. 3. As shown in FIG. 4, the gel pad 42 is laterally enclosed by the inner walls of front aperture pad 40. With spacer pad 22 removed from the surface of unit 44, the surface of the gel layer 42 extends beyond the surface of front pad 40. This is better shown in FIGS. 5 and 6.

Figure 5:
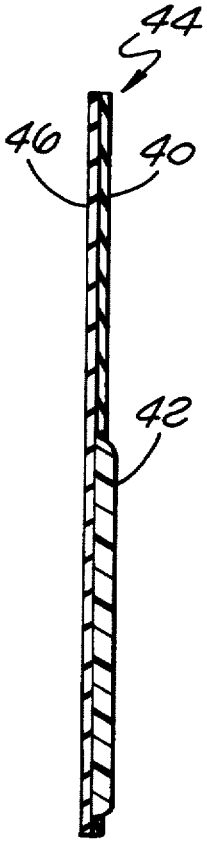
FIG. 5 is a cross-sectional view taken along the line 5—5 of FIG. 4, illustrating the back pad, front aperture pad, and the semi-solid gel layer.

FIG. 5 is a cross-sectional view of the gel liner 44, viewed along the lines V—V of FIG. 4, illustrating the back pad 46, front aperture pad 40, and the semisolid gel layer 42. As clearly shown in FIG. 5, the gel layer 42 is thicker than from pad 40, as a result of the use of the spacer pad. This provides for a more efficient and comfortable gel pad that easily conforms to the shape of the ankle for a firm and resilient support of the injured ankle. These individual units of gel linen may easily be used in a walking brace 52 as shown in FIG. 7. Further, a portion of the gel pad 42 is laterally enclosed by the inner walls of the from aperture pad, to provide increased strength to the assembly. This is better shown in FIG. 6 of the drawings.

Figure 6:
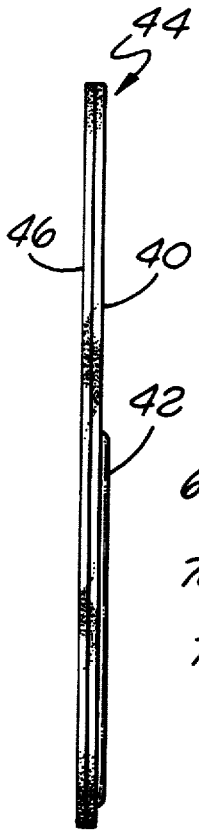
FIG. 6 is a side view of the get pad of FIG. 4, illustrating the manner in which the gel pad is confined to the back pad, and inner walls of the front pad.
Figure 7:
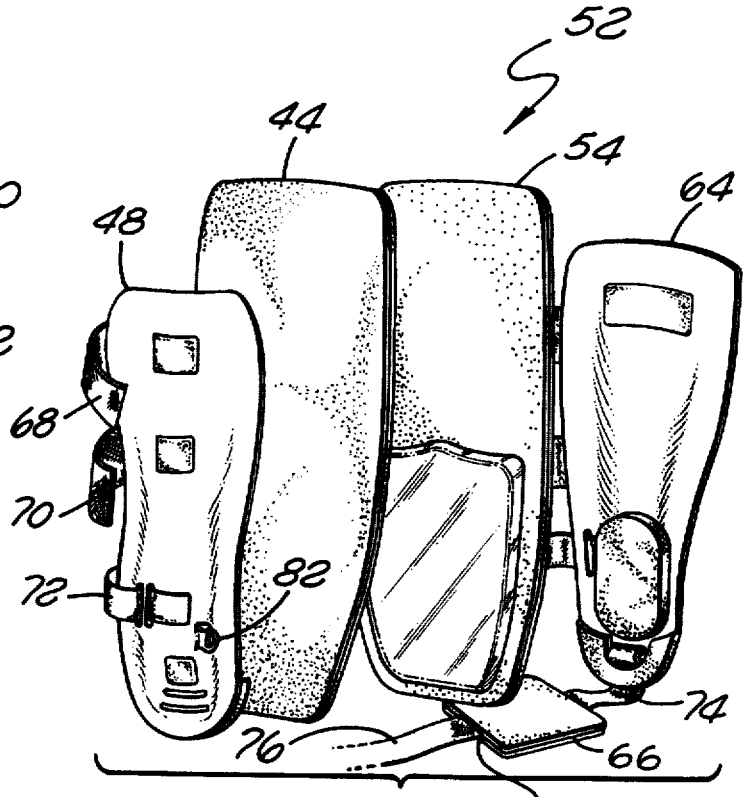
FIG. 7 is a perspective view of a walking brace assembly, illustrating the manner in which the individual units of gel-pads are used in the walking brace.

FIG. 6 is a side view of the gel liner 44 of FIG. 5, further illustrating the relative position of the different layers of the gel liner 44. As shown, a portion of the gel pad 42 is laterally confined by the inner walls of the front pad 40.

FIG. 7 is an exploded view of a walking brace 52 illustrating the manner in which the individual units of gel liners 44 and 54 are used in walking brace 52. Each of the gel pads 44 or 54 are used to provide for a resilient support against the ankle on each side of the leg. Gel liner 54 may be attached to the support wall 64 using velcro type material or other similar means. Similarly, gel liner 44 may be attached to the support wall 48 using [Velcro] *VELCRO* type material or other similar means. As is known in the art, [VELCRO type material] *hook and loop material, such as VELCRO,* includes one pad having a series of very small hooks mounted on its surface, and another mating pad having loops or similar fabric configuration on its surface, in which the loops may engage. The two gel pads 44 and 54 and the stiff support walls 48 and 64 each have two matching Velcro pads, see pads 65 and 67 on support wall 64, and pads 69 and 71 on gel pad unit 44. The gel pad units and the support walls may also have oppositely paired VELCRO pads at their top and bottom so that the gel pads may not be mounted on the side walls upside down.

To further support the leg, a U-shaped stirrup member 80 is used. Stirrup member 80 includes a base plate or pad member 66 and straps 74 and 76. The base plate or pad member 66 extends underneath the heel of the user. The straps 74 and 76 are used for firmly attaching the base plate 66 to the side wall supports 64 and 48, respectively. Thus, for example, strap 76 extends in and out of slots 73 and 75, respectively and engages [Velcro] *VELCRO* pad 77.

The side support walls 48 and 64 may better support the leg when a counter strap 72 is used just above the heel to further limit the side wails 64 and 48 from moving outward relative to the ankle. In addition, the bottom portion of the side wails 48 and 64 may be inserted in a shoe. With the bottom portion of the walking brace inserted in the shoe, the lace fastening loops 82 and 84 my be used to tightly secure the brace on the foot in the ankle area. This is done by passing the shoe lace through the D-shaped loop members 82 and 84 and then bringing the shoe laces back to the front and tying them together.

Figure 8:
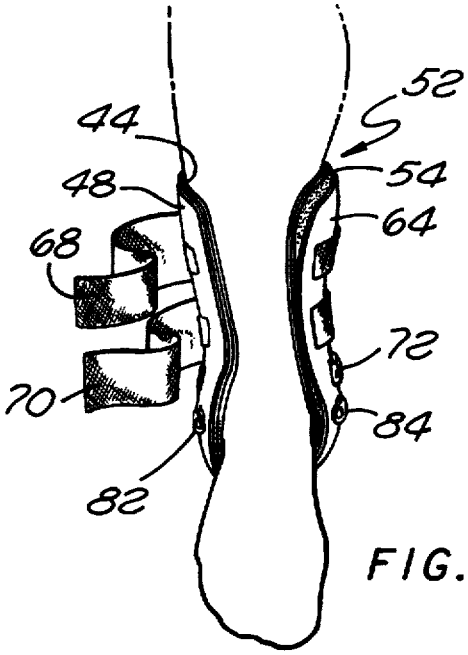
FIG. 8 illustrates the manner in which the gel pads and the walking brace support the ankle.

FIG. 8 illustrates the manner in which the walking brace is put on, with the gel pads providing a comfortable, firm and resilient support against the ankle. As shown, the liners 52 and 44 substantially conform to the shape of the leg. Further, the side support wails 64 and 48 provide for a firm support against the leg. The straps 68 and 70 are used to firmly hold the walking brace around the leg. This is better shown in FIG. 9.

Figure 9:
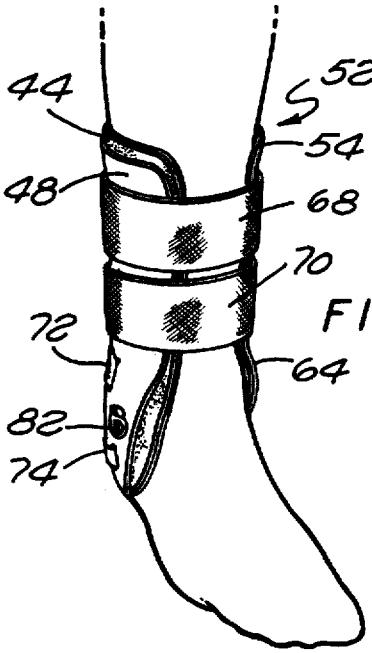
FIG. 9 illustrates the manner in which the straps on a walking brace are used to provide a firm grip around the leg, with the gel pads resiliently supporting the ankle.

FIG. 9 illustrates the manner in which a walking brace is secured. As shown, the upper pan of the leg is firmly supported using the straps 68 and 70. The mid and lower portion of the leg is supported by strap 70 and counter strap 72. The lower portion of the leg is supported by the counter strap 72 and lace members 82, 84, and the U-shaped stirrup member 80.

The pad shown in FIG. 10 is similar to that shown and described hereinabove in connection with FIGS. 4 through 7. More specifically, the pad of FIGS. 10 and 11 includes a foam rubber backing pad 102, a central gel pad 104, and a peripheral layer of foam 106 which essentially merely forms an enclosing rim, following cutting from a larger sheet. In addition, it may be noted that the gel pad 104 includes a recess 108 in the vicinity of the ankle bone, or malleolus. In addition, a thin polyurethane film 110 extends over the lower surface of the gel pad 104, as shown in FIG. 11, and is bonded to the backing layer 102 and to the peripheral foam layer 106. In order to form the recess 108, a small rounded member may be placed on the apertured plate 20, as shown in FIGS. 1 and 2, in the proper location, to form the desired recess, as the urethane film is laid over the apertured layers in the manner discussed hereinabove.

FIGS. 12, 13, and 14 disclose the use of a gel pad assembly 122 which is shown as providing heat or cold therapy to the back of a person's neck, see particularly FIG. 14. In FIG. 14, the gel pad 122 is held in place by a neck restraint 124 which extends around a person's neck, and is held by suitable interfitting VELCRO pads, at the throat. As well as providing additional restraint, the pad 122 my be employed to provide hot or cold therapy, as may be advised by a doctor. Hot therapy may be achieved by heating the gel pad 122 in a microwave oven for a few seconds, to the desired temperature; and cold therapy may be accomplished by precooling the unit 122 in a refrigerator or freezer.

As shown to advantage in FIG. 13, taken along line 13—13 of FIG. 12, the assembly 122 includes a backing layer 126 of a thin film of polyurethane material, and a front layer 128 also of urethane film, bonded to the rear layer 126 along the periphery 130 of the unit, and also at areas, such as the area 132, between adjacent gel pad areas 134 and 136, for example. As shown in FIG. 12, the pad 122 also includes additional gel pad zones 138, 140, 142, and 144.

If desired, the assembly 122 may be provided with a Velcro pad 152 which may make mating engagement with a mating [Velcro] *VELCRO* pad on the central rear area of the neck brace 124. The VELCRO pad 152 is preferably of the hook type, while the mating pad on the neck brace 124 may be of the loop type, which is relatively soft, and which will not cause discomfort, if the neck brace 124 is employed without the additional gel pad supporting member 122.

The gel pad member 122 may be fabricated using the apertured plate and vacuum arrangements of FIGS. 1 and 2, and employing a ridged spacer member, such as the member 22 shown in FIGS. 1 and 2, but formed to provide the recessed areas, such as the area 132 which separates the various gel pad areas, as shown in FIGS. 12 and 13. With this type of recessed configuration, the assembly 122 may readily have its outer edges bent up out of the plane of the paper, in the showing of FIG. 12, so that it will easily fit around the neck and the back of the head, as shown in FIG. 14.

Accordingly, it may be seen that the use of the urethane layer, in combination with the gel pad, gives considerable advantages and flexibility in the formation of the gel pad to the desired configuration. This advantage is in addition to its supplemental functions of avoiding undesired flow of the gel onto the patient; and conversely, the urethane layer prevents contamination of the gel included in the medical orthopaedic product.

The gel used in the implementation of the present invention is preferably of the type sold under the trademark ELASTO-GEL, by Southwest Technologies, Inc. of Kansas City, Mo. Attention is also directed to Edward I. Stout, U.S. Pat. No. 4,671,267, granted Aug. 1, 1986, which discloses the method for making the gel. In practice, the gel is mixed in liquid form and must be poured promptly into the pockets 27 for receiving gel as shown in FIG. 1 of the drawings, where it hardens to a semi-solid state within about 1 to 5 minutes.

Concerning dimensions, the gel pad assemblies as shown in FIGS. 4, 5 and 6 may be in the order of ten or eleven inches in length and about 3 and one-half to 4 and one-half inches in width. The actual gel portion of the pad may be about three inches in width and about five inches in length. The pad unit as a whole is about one-quarter inch thick, with the gel portion protruding by about one-sixteenth inch. In one embodiment, the gel pad extends over most of the area of the unit of FIGS. 4, 5 and 6, with the front layer only forming a rim about one-quarter to one-half inch wide around the periphery. In another embodiment, no foam rubber layers were present in the unit; instead, a thicker spacer layer having a larger size opening was used, and a urethane film was used for the backing sheet. The resultant gel pad was similar in its overall configuration to the pads shown in my copending patent application cited hereinabove.

Concerning the gel pads, the combination of the inner gel pads and outer stiff supporting members, such as the plastic supports 48 and 64, or aluminum splinting stays, for example, has certain unique advantages. Specifically, these advantages include:

1. Hot and cold therapy resulting from the high specific heat or thermal capacity of the gel, and its resultant quality of being able to supply heat or cooling to an injured member, by pre-heating or precooling the gel pad, before application.

2. Conformation of the gel pad to the user's bodily configuration. The gel pad has semi-solid gel which becomes deformed during use, and retains its deformed configuration to a substantial extent. Thus when a user takes the brace off, and then uses it again, putting it back on the ankle, wrist, or other pan of the anatomy, the gel pad already conforms substantially to the shape of the anatomy and an immediate comfortable fit results.

3. The gel pad is self-sealing as compared with air-inflatable cushion arrangements, so that injury from the stiff supporting members cutting or rubbing the user, cannot occur.

4. The gel is not U.V. sensitive, and therefore does not deteriorate when subject to prolonged U.V. exposure.

It is noted in passing that the invention is not limited to the embodiment shown in the drawings or to the foregoing detailed description. By way of example and not of limitation, the spacer pad, front pad, and back pad may be made of flexible foam rubber material, or other flexible material. Alternatively, the spacer pad may be made of solid and inflexible material. The thickness of these pads may be relatively small, for example 3 millimeters. The thickness of the three pads may be substantial equal or may be different. The back pad or rear closure may be very thin and made of flexible material. For example, the backing layer may be made of a thin plastic film, such as the urethane film 26, and the two urethane films may then be heat bonded or adhesively sealed to one-another to confine the gel. When the gel pad is confined by urethane film, front and back, a thicker spacer pad may be used so that the gel pad remains fairly thick, and may have no front pad. Apertures may have various patterns to meet the needs of a particular application. The apertures may have a definite geometrical shape, for example, a rectangular shape, a horseshoe shape, or they may have curved boundaries to match the desired orthopaedic soft goods application. The thin film may be made of urethane or other suitable thin and flexible material. The vacuum chamber may be wooden, plastic or may be made of other suitable material. The holes on the perforated base plate may be substantially equal in size ranging from less than one to more than five millimeters in diameter. The holes may have uneven diameter sizes. Further, the holes may be evenly distributed throughout the base plate, or preferably, they may outline the inner edge of the spacer pad openings, with different perforated base plates being employed for differently shaped gel pads. The pattern on the surface of each of the pads may vary according to particular needs of an application.

What is claimed is:

1. A reusable orthopaedic brace or support comprising:

a gel pad assembly including a layer of gel;

said gel pad assembly having an impervious thin front plastic film directly engaging and confining the gel in said gel pad assembly, for preventing contamination thereof and for preventing flow of said gel onto the user;

a backing layer extending across the rear of said gel, to confine said gel, and to prevent contamination thereof, said front plastic film being permanently bonded to said backing layer, orthopaedic support means for holding said gel pad assembly against a portion of the anatomy of a user;

said plastic film defining the shape of the gel layer of said gel pad assembly and the thickness of the gel relative to said backing layer;

said gel pad assembly having a forwardly extending front surface which is formed of relatively flat gel material covered by said plastic film, and said assembly having other areas facing in the same direction as said front surface which are recessed back from said front surface;

said assembly permanently sealing the gel between the impervious front plastic film and the backing layer; and a peripheral enclosing aperture pad secured to said backing layer and extending around and enclosing the sides of the gel, while the gel and said plastic film extend forward from a plane defined by the front surface of said aperture pad.

2. An orthopaedic brace or support assembly as defined in claim 1 wherein said backing layer is formed of a sheet of foam rubber.

3. A reusable ankle brace for insertion into a shoe for immobilizing the ankle against inversion and eversion while permitting planter-flexion and dorsi-flexion, comprising:

a pair of stiff side supports for fitting about the lower leg on both sides;

said side supports having a configuration to encompass both sides of the ankle, with the lower end of the side supports for insertion into the sides of the shoe;

a pair of liner members including a layer of dense gel for conforming to the shape of the ankle and for providing a resilient support against the ankle; each said liner member including an apertured front pad having a patterned opening, an impervious thin film, a resilient backing pad, a semi-solid gel layer enclosed between said backing pad and said thin film, adhesive means for holding said thin film, said front pad, and said backing pad firmly and permanently together with said gel layer permanently enclosed between said thin film and said backing layer;

means for securing each said liner member to each said side support wall; and means for securing said side supports to firmly encase the ankle, said means including a counter strap extending between said side supports at a position just above the heel, said means also including a U-shaped stirrup member for providing a tighter grip about the lower portion of the leg; said means also including at least one strap extending between said side supports for firmly encasing and supporting the top and middle portion of the leg.

4. An apparatus as defined in claim 3 wherein said front pad and said backing pad each include a layer of foam rubber.

5. An apparatus as defined in claim 3 wherein said backing pad includes a thin layer of urethane.

6. A reusable orthopaedic brace or support comprising:

a gel pad assembly including a layer of gel;

said gel pad assembly having an impervious front plastic film for confining the gel in said gel pad assembly, for preventing contamination thereof and for preventing flow of said gel onto the user;

a backing layer extending across the rear of said gel, to confine said gel, and to prevent contamination thereof, said front plastic film being permanently bonded to said backing layer, said plastic film defining the shape of the gel layer of said gel pad assembly and the thickness of the gel relative to said backing layer;

said gel pad assembly having a forwardly extending front surface which is formed of relatively flat gel material covered by said plastic film, and said assembly having other areas facing in the same direction as said front surface which are recessed back from said front surface;

said gel layer being formed into a plurality of zones by the engagement of said film with said backing layer; and orthopaedic support means for holding said gel pad assembly against the back of a person's neck to preclude excessive movement of the head.

7. A reusable orthopaedic brace or support including a gel pad assembly comprising:

a first continuous substantially flay backing foam sheet member;

a second substantially flat foam sheet member having an opening through it;

a layer of gel mounted in said opening and extending outwardly away from said two foam sheet members;

a thin impervious film of sheet material extending over the outwardly extending gel layer, and said film extending in through the opening around the periphery of the gel layer to confine it, while facilitating heat flow between the gel layer and the body of a user;

means for permanently securing said two foam layers together and to said thin film to form a resilient gel pad assembly with said gel layer covered by said impervious thin film protruding outwardly from the two foam layers and from said assembly; and support means for holding said gel pad assembly against a portion of the body of the user and for limiting movement of the body of the user.

8. An orthopaedic brace for support as defined in claim 7 wherein the outer edges of said thin film are permanently secured in place between said two foam sheet members.

9. A reusable orthopaedic brace or support comprising:

a gel pad assembly including a layer of gel;

said gel pad assembly having an impervious thin front plastic film directly engaging and confining the gel in said gel pad assembly, for preventing contamination thereof and for preventing flow of said gel onto the user;

a backing layer extending across the rear of said gel, to confine said gel, and to prevent contamination thereof, said front plastic film being permanently bonded to said backing layer, orthopaedic support means for holding said gel pad assembly against a portion of the anatomy of a user;

said plastic film defining the shape of the gel layer of said gel pad assembly and the thickness of the gel relative to said backing layer;

said gel pad assembly having a forwardly extending front surface which is formed of relatively flat gel material covered by said plastic film, and said assembly having other areas facing in the same direction as said front surface which are recessed back from said front surface;

said assembly permanently sealing the gel between the impervious front plastic film and the backing layer;

said gel pad assembly including two separate gel pads; and means including two stiff plastic members for holding said gel pads against the inner and outer sides of a patient's ankle.

10. A reusable orthopaedic brace or support comprising:

a gel pad assembly including a layer of gel;

said gel pad assembly having an impervious thin front plastic film for confining the gel in said gel pad assembly, for preventing contamination thereof and for preventing flow of said gel onto the user;

a backing layer extending across the rear of said gel, to confine said gel, and to prevent contamination thereof, said front plastic film being permanently bonded to said backing layer, orthopaedic support means for holding said gel pad assembly against a portion of the anatomy of a user;

said plastic film defining the shape of the gel layer of said gel pad assembly and the thickness of the gel relative to said backing layer, and permanently confining said gel between said film and said backing layer; and a peripheral enclosing aperture pad secured to said backing layer and extending around and enclosing the sides of the gel, while the gel and said plastic film extend forward from a plane defined by the front surface of said aperture pad.

11. A reusable orthopaedic brace or support comprising:

a gel pad assembly including a layer of gel;

said gel pad assembly having an impervious thin front plastic film for confining the gel in said gel pad assembly, for preventing contamination thereof and for preventing flow of said gel onto the user;

a backing layer extending across the rear of said gel, to confine said gel, and to prevent contamination thereof, said front plastic film being permanently bonded to said backing layer, orthopaedic support means for holding said gel pad assembly against a portion of the anatomy of a user;

said plastic film defining the shape of the gel layer of said gel pad assembly and the thickness of the gel relative to said backing layer, and permanently confining said gel between said film and said backing layer;

said gel pad assembly including two separate gel pads; and means including two stiff plastic members for holding said gel pads against the inner and outer sides of a patient's ankle.

12. A reusable orthopaedic brace or support comprising:

a resilient substantially flat backing sheet;

an apertured front pad;

a substantially flat semi-solid gel pad layer mounted in the aperture in said front pad and protruding forward and away from said backing sheet and front pad;

a substantially impervious thin film adhesively and permanently secured between said backing sheet and said front pad and extending over the front of said gel pad layer;

stiff orthopaedic support means for holding said gel pads in engagement with a portion of a patient's body;

said stiff support means includes two relatively movable parts; and removable securing means including strap means for firmly holding said two relatively movable parts together.

*13. A reusable orthopaedic brace or support assembly comprising:*

*an orthopaedic support for extending around an injured portion of a user's body;*

*means including a gel pad for applying hot and cold therapy to the injured portion of the user's body;*

*said gel pad having an impervious thin front plastic film means directly engaging and confining the gel within said gel pad, for preventing contamination thereof, for preventing flow of said gel onto the user, and for facilitating heat transfer for said hot and cold therapy;* a backing layer extending across the rear of said gel, to confine said gel, and to prevent contamination thereof, said front plastic film means being secured to said backing layer;

*quick release securing means for holding said pads onto said orthopaedic support;*

*said orthopaedic support having a configuration conforming to the irregular configuration of the portion of the user's body to which the assembly is being applied; and*

*means for holding said orthopaedic support and said gel pad firmly onto the injured portion of the user's body;* whereby the injured portion of the user's body may be concurrently provided with support and said hot and cold therapy, with the gel pads pressed against the injured portion.

*14. A reusable orthopaedic brace or support comprising:*

*a gel pad assembly including a layer of gel for providing hot and cold therapy;*

*said gel pad assembly having an impervious thin front plastic film means for confining the gel in said gel pad assembly, for preventing contamination thereof, for preventing flow of said gel onto the user, and for facilitating heat transfer for said hot and cold therapy;*

*a backing layer extending across the rear of said gel, to confine said gel, and to prevent contamination thereof, said front plastic film means being permanently bonded to said backing layer; and*

*orthopaedic support means for holding said gel pad assembly against a portion of a user's body.*

*15. A reusable orthopaedic brace or support as defined in claim 14, further including quick release securing means for holding said pads onto said orthopaedic support.*

*16. A reusable orthopaedic brace or support as defined in claim 14, in which the orthopaedic support has a configuration conforming to the irregular configuration of the portion of the user's body to which the assembly is being applied.*

*17. A reusable orthopaedic brace or support comprising:*

*a gel pad assembly including a layer of gel for providing hot and cold therapy;*

*said gel pad assembly having an impervious thin front plastic film for confining the gel in said gel pad assembly, for preventing contamination thereof, for preventing flow of said gel onto the user, and for facilitating heat transfer for said hot and cold therapy;*

*a backing layer extending across the rear of said gel, to confine said gel, and to prevent contamination thereof, said front plastic film being permanently bonded to said backing layer;*

*orthopaedic support means for holding said gel pad assembly against a portion of a user's body; and*

*quick release securing means for holding said pads onto said orthopaedic support;*

*in which the orthopaedic support has a configuration conforming to the irregular configuration of the portion of the user's body to which the assembly is being applied.*

*18. An orthopaedic brace or support assembly, comprising:*

*a gel pad assembly including (1) a body of gel adapted to provide hot and cold therapy too an injured portion of a user's body, (2) an impervious thin front film which extends across a front of said body of gel, which prevents flow of the gel of said body of gel onto the user and which facilitates the transfer of therapeutic heat and cold from said body of gel to the injured portion, and (3) a backing layer extending across a rear of said body of gel and secured to said front film to thereby confine and protect said body of gel; and*

*orthopaedic support means for holding said gel pad assembly with said front film generally against the injured portion such that hot and cold therapy can be applied to the injured portion.*

*19. An apparatus as defined in claim 18 wherein said front film is constructed of plastic and is permanently sealed to said backing layer.*

*20. An apparatus as defined in claim 18 wherein said backing layer is constructed so to resiliently support the injured portion and to thermally insulate the rear of said body of gel.*

*21. An apparatus as defined in claim 18 wherein said orthopaedic support means includes a support member configured to conform to the irregular configuration of the part of the user to which said apparatus is being applied.*

*22. An apparatus as defined in claim 18 wherein said front film permits configuration of said body of gel to a contour of the injured portion.*

*23. An apparatus as defined in claim 18 wherein said front film is formed of urethane.*

*24. An apparatus as defined in claim 18 wherein said gel pad assembly self seals after a puncture thereto.*

*25. An apparatus as defined in claim 18 wherein said body of gel includes a semi-solid gel which deforms during use against the injured portion and retains its deformed configuration to a substantial extent after removal from the injured portion such that said assembly is reusable thereon.*

*26. An apparatus as defined in claim 18 further comprising quick release securing means for releasably securing said gel pad assembly to said orthopaedic support means.*

* * * * *